US010828272B2

(12) United States Patent
Broekkamp et al.

(10) Patent No.: US 10,828,272 B2
(45) Date of Patent: Nov. 10, 2020

(54) MEANS TO FACILITATE FOOD INTAKE AND FOOD RETENTION

(71) Applicant: Chardon Group B.V., Herpen (NL)

(72) Inventors: Christophorus Louis Eduard Broekkamp, Oss (NL); Bernardus Wijnand Mathijs Marie Peeters, Herpen (NL)

(73) Assignee: Chardon Group B.V., Herpen (NL)

( * ) Notice: Subject to any disclaimer, the term of this patent is extended or adjusted under 35 U.S.C. 154(b) by 37 days.

(21) Appl. No.: 14/401,358

(22) PCT Filed: May 15, 2013

(86) PCT No.: PCT/EP2013/060013
§ 371 (c)(1),
(2) Date: Nov. 14, 2014

(87) PCT Pub. No.: WO2013/171252
PCT Pub. Date: Nov. 21, 2013

(65) Prior Publication Data
US 2015/0133502 A1   May 14, 2015

(30) Foreign Application Priority Data

May 16, 2012  (EP) .................................. 12075046

(51) Int. Cl.
| *A61K 31/167* | (2006.01) |
| *A61K 9/08* | (2006.01) |
| *A61K 31/445* | (2006.01) |
| *A61K 9/00* | (2006.01) |

(52) U.S. Cl.
CPC .......... *A61K 31/167* (2013.01); *A61K 9/0019* (2013.01); *A61K 9/0053* (2013.01); *A61K 9/08* (2013.01); *A61K 31/445* (2013.01)

(58) Field of Classification Search
CPC ... A61K 31/167; A61K 9/0053; A61K 31/445
USPC ................................................. 514/330, 626
See application file for complete search history.

(56) References Cited

U.S. PATENT DOCUMENTS

| 5,810,786 | A  | * | 9/1998 | Jackson | .................. | A61F 13/00 |
| | | | | | | 604/265 |
| 6,299,902 | B1 | * | 10/2001 | Jun | ...................... | A61K 9/0014 |
| | | | | | | 424/443 |
| 2008/0021068 | A1 | * | 1/2008 | Alam | .................... | A61K 9/0048 |
| | | | | | | 514/331 |
| 2009/0036490 | A1 | * | 2/2009 | Verity | .................. | A61K 9/0014 |
| | | | | | | 514/330 |

FOREIGN PATENT DOCUMENTS

| JP | 2008094743 | * | 4/2008 | |
| WO | WO 2012146763 | A1 | * | 11/2012 | ............. A61K 45/06 |

OTHER PUBLICATIONS

Gaziano, Evaluation and Management of Oropharyngeal Dysphagia in Head and Neck Cancer; Cancer Control 9(5):400-409, 2002.*
Bardy et al., A double-blind, placebo-controlled, randomized trial of active Manuka honey and standard oral care for radiation-induced oral mucositis, British Journal of Oral and Maxillofacial Surgery 50 (2012) 221-226.*
Mosegor Novartis, Pharma Guide, 2007 (Year: 2007).*
Hardie et al., Evaluation of intermittent infusion of bupivacaine into surgical wounds of dogs postoperatively, The Veterinary Journal 190 (2011) 287-289 (Year: 2011).*
Henriksen et al., Early Oral Nutrition After Elective Colorectal Surgery: Influence of Balanced Analgesia and Enforced Mobilization, Nutrition 2002;18:263-267, Elsevier Science Inc. 2002 (Year: 2002).*
Chee et al., The Influence of Chemical Gustatory Stimuli and Oral Anesthesia on Healthy Human Pharyngeal Swallowing, Chem. Senses 30: 393-400, 2005 (Year: 2005).*
Sachan et al., Sodium alginate: the wonder polymer for controlled drug delivery, Journal of Pharmacy Research 2009, 2(8),1191-1199 (Year: 2009).*
Owen et al., Ropivacaine, Expert Opinion on Pharmacotherapy, 1:2, 325-336, Abstract only (Year: 2000).*
Chrubasik et al., Efficacy of a benzocaine lozenge in the treatment of uncomplicated sore throat, Eur Arch Otorhinolaryngol (2012) 269:571-577; published online Oct. 21, 2011. (Year: 2011).*
Kolawole et al., Post-Anaesthetic Respiratory Complaints Following Endotracheal Anaesthesia in Lower Abdominal Obstetric and Gynaecology Surgery, Nigerian Journal of Clinical Practice Sep. 2008 vol. 11(3) :225-230. (Year: 2008).*
Communication pursuant to Article 94(3) EPC, dated Nov. 25, 2016, for corresponding European Application No. 13724779.7.
Balfour, Jr. D. C. et al., "Use of Procaine Hydrochloride by Mouth for Gastrointestinal Disorders," Gastroenterology, Elsevier, Amsterdam, NL, vol. 22, No. 2, Jan. 1, 1952 (Jan. 1, 1952), pp. 257-262, XP009192489.
Silk, A.D. et al., "The Use of Oral Procaine in a Case of 'Lysol' Poisoning", Gastroenteroly, Elsevier, Amsterdam, NL, vol. 23, No. 2, Jan. 1, 1953 (Jan. 1, 1953), pp. 301-303, XP009192488.

(Continued)

*Primary Examiner* — Frederick F Krass
*Assistant Examiner* — Nabila G Ebrahim
(74) *Attorney, Agent, or Firm* — F. Aaron Dubberley

(57) ABSTRACT

The disclosure provides for means for a method to facilitate food intake and food retention in a mammal by applying a sufficient dose of a local anesthetic drug in the lumen of the pharyngeal-esophageal-gastric-duodenal tract before or during or after eating. The local anesthetic can be amethocaine, articaine, benzocaine, bupivacaine, chloroprocaine, cinchocaine, cyclomethycaine, dibucaine, diethocaine, etidocaine, larocaine, levobupivacaine, lidocaine, lignocaine, mepivacaine, novocaine, piperocaine, prilocaine, procaine, proparacaine, propoxycaine, QX-222, QX-314, ropivacaine, tetracaine, trimecaine, menthol, eugenol or a safe pharmaceutical formulations of tetrodotoxin, saxitoxin, or neosaxitoxin. The disclosure is useful for patients having problems with food intake or food retention.

21 Claims, No Drawings

(56) References Cited

OTHER PUBLICATIONS

Damien Mcnally et al., "Randomised, Double-Blind, Placebo-Controlled Study of a Single Dose of an Amylmetacresol/2,4-dichlorogenzyl Alcohol Plus Lidocaine Lozenge or a Hexylresorcinol Lozenge for the Treatment of Acute Sore Throat Due to Upper Respiratory Tract Infection," Journal of Pharmacy and Pharmaceutical Sciences, vol. 15, No. 2, Apr. 2, 2012 (Apr. 2, 2012), pp. 281-294, XP055321266.

Joy E. Garziano, "Evaluation and Management of Oropharyngeal Dysphagia in Head and Neck Cancer," Cancer Control, vol. 9, No. 5, Sep. 1, 2002 (Sep. 1, 2002), pp. 400-409, XP055320401.

Joy Bardy et al., "A Double-Blind, Placebo-Controlled, Randomised Trial of Active Manuka Honey and Standard Oral Care for Radiation-Induced Oral Muscositis," British Journal of Oral and Maxillofacisl Surgery, vol. 50, No. 3, Jun. 1, 2011 (Jun. 1, 2011) pp. 221-226, XP055321342.

Public Assessment Report of the Medicines Evaluation Board in the Netherlands for Trachisan 8 mg, lozenges. Date of first publication Mar. 29, 2009. Last revision Oct. 11, 2010.

Directions for Use for Benylin Sore Throat Lozenges, https://www.benylin.ca/products/sore-throat-lozenge/sore-throat-lozenge, as accessed Apr. 7, 2020.

* cited by examiner

MEANS TO FACILITATE FOOD INTAKE AND FOOD RETENTION

CROSS-REFERENCE TO RELATED APPLICATION

This Application is a Section 371 National Stage Application of International Application No. PCT/EP2013/060013, filed May 15, 2013 and published as WO 2013/171252 A1 on Nov. 21, 2013, in English.

BACKGROUND

The discussion below is merely provided for general background information and is not intended to be used as an aid in determining the scope of the claimed subject matter.

This disclosure relates to means for use in a method to facilitate food intake and food retention in a mammal and to a local anesthetic and a pharmaceutical formulation thereof for application on a pharingeal-esophageal-gastric-duodenal mucous surface of a mammal.

This disclosure addresses medical problems related to reduced food intake despite sufficient availability of food. Those problems are the main symptoms occurring in disorders such as anorexia, cachexia, sarcopenia, postoperative ileus and postoperative complications in food processing.

Anorexia-cachexia is reduced food intake and reduced utilization of ingested food. It is an illness that may occur in terminal stages of many chronic illnesses including cancer, chronic heart failure, chronic renal failure or chronic obstructive pulmonary disease.

Sarcopenia is general deterioration of muscle mass and quality occurring at old age. It is believed that the lack of exercise and loss of appetite are important characteristics of sarcopenia or frailty at old age. Postoperative ileus is decreased motor activity of the GI tract unrelated to any mechanical cause. It can occur often as a postoperative complication of abdominal surgery. After surgery the start of food intake is a delicate moment in recovery. The optimum moment of starting intake of solid food is important for recovery, whereby early acceptance of a solid meal at the proper moment is helpful in initiating all the processes involved in digestion, including intestinal motility, that is, it improves resumption of food transit and recovery.

Current medicinal treatments of mentioned disorders are based on anabolic enhanced protein formation or on stimulation of intestinal motility by a prokinetic drug, such as metoclopramide. Other therapeutic approaches explored currently for anorexia-cachexia disorders are treatment with melanocortin-4 receptor antagonists, myostatin inhibition, beta-blockers, IL-6 antagonism, synthetic ghrelin and vitamin D.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present invention provides for a method to facilitate food intake and food retention in a mammal by applying a sufficient dose of a local anesthetic drug in the lumen of the pharyngeal-esophageal-gastric-duodenal tract before, during or shortly after eating. The facilitation of food intake and food retention can be an increase in the size of a meal, an increase in the frequency of meals or a better acceptance, tolerance, intake and/or retention of food. A mammal can be a human person. An aspect of the invention is preferably used for human patients.

DESCRIPTION

Without committing to a particular explanation, we believe that the facilitation is brought about by reduction of signals originating in the tissue layers facing the lumen of the pharynx, esophagus, stomach and/or duodenum. Such signals provide the organism information to determine food intake, for example for initiation, termination or prolongation of a meal. Signals arising from these tissues can contain information on the quality or amount of food having passed the pharynx or esophagus, or the quality or amount of food being present in the stomach or duodenum. Meal size in particular is determined by satiety signals arising from different receptors in brain and gastrointestinal tract. For example, the duodenum signals filling with food and produces cholecystokinin. Cholecystokinin passes the signal to the afferent vagus nerve, which passes the information to the brain in order to terminate eating. A similar signal originating from the gastrointestinal tract is arising from glucagon-like peptide which is produced in the gastro-intestinal cell wall and activates the vagus afferents. Further signals are transmitted to the brain by the vagus nerve arising from the degree of stomach distension measured by stretch receptors in the wall of the stomach. Other hormones that control digestion and eating behavior are gastrin and secretin. Another important hormone for regulating appetite is ghrelin, which is produced in the stomach and upper intestine in the absence of food in the digestive system and stimulates appetite. Peptide YY is produced in the digestive tract in response to a meal in the system and inhibits appetite. Other hormones are also studied that may play a part in inhibiting appetite, including leptin, oxyntomodulin (+), and pancreatic polypeptide. We do not have a complete and certain explanation for the mechanism of action of the local anesthetic in facilitating food intake and retention. It may be that satiety signals originating from the surface of the pharynx, esophagus, stomach and/or duodenum are blunted by the local anesthetic and that this incites the treated subject to postpone termination of a meal. Another possibility is that the local anesthetic reduces an aversive or repulsive signal arising from some constituents in food, and which constituents or signals would normally inhibit further intake or even initiate repulsion or sensations of aversion influencing the future perception of same or similar food.

Some observations of effects of local anesthetics on stomach or esophagus in the context of food intake were described in the prior art, without the possibility to derive from those observations the effect disclosed in the present description. Uneyama et al. (Am. J. Physiol.—Gastrointestin. & Liver Physiol., Vol 291, pp 1163-1170, 2006) described chemosensing of glutamate in the stomach wall, signaled to the central nervous system by the gastric branch of the vagus nerve. Uneyama reported that this chemosensing signal can be blocked by lidocaine. However, it is known that glutamate in food induces overeating so Uneyama's result could suggest, if anything on food intake, a reduction of food intake by blunting the signal arising from chemosensing glutamate. Chee et al (Chemical Senses, Vol 30, pp 393-400, 2005) reported on observations on the effect of local anesthetic on the pharynx on eating and swallowing. It was observed that swallowing speed was reduced, swallowing interval prolonged and swallowing capacity unchanged, leading to the conclusion of the authors of this disclosure that chemosensory input influenced swallowing function.

The effect obtained from the disclosure has the advantage to facilitate food intake and retention also under circumstances that the treated subject is not inclined to eat a particular food although that type of food would be particularly healthy for the treated subject under the circumstances. Thus, in combination with nutrients of optimal composition the treated subject can gain strength and recover from lack of appetite.

There are various medical conditions and circumstances in which a treated subject will benefit from the effect obtained from the disclosure. Patients with various causes for lack of appetite or lack of motivation to eat a sufficiently sized meal will benefit from the present disclosure. In particular in the elderly population and patients in various nutrient-depleted conditions of disease require stimulation of food intake. By taking a meal of sufficient size the further processing functions of the digestive system will also be stimulated, such as intestinal motility and secretion of digestion stimulating juices and hormones. Such patients can be diagnosed as suffering from anorexia, cachexia, sarcopenia or postoperative ileus. Also, a postoperative period shortly following on surgery is a period during which it can be helpful to use the effect obtained from the present invention. In particular after surgery on the intestinal tract or after ceasarian section early postoperative feeding is helpful for recovery. Under those circumstances recovery is assisted if a patient has solid food in the digestive tract in order to improve resumption of food transit by stimulating in time the process of intestinal motility and any other processes important for digestion. Early postoperative feeding aided by use of local anesthetic according to the method disclosed in this specification can prevent postoperative gastroparesis syndrome (PGS) and it can prevent postoperative nausea and vomiting (PONV). Currently metoclopramide is often used in those circumstances. However this compound has a narrow therapeutic window for this use and requires systemic administration so that the drug is present in the whole organism. In contrast, the effective concentration of a local anesthetic used according to the present invention can remain restricted to the luminal surface of the upper parts of the digestive tract.

Local anesthetics that can be used according to this invention are: amethocaine, articaine, benzocaine, bupivacaine, chloroprocaine, cinchocaine, cyclomethycaine, dibucaine, diethocaine, etidocaine, larocaine, levobupivacaine, lidocaine, lignocaine, mepivacaine, novocaine, piperocaine, prilocaine, procaine, proparacaine, propoxycaine, QX-222, QX-314, ropivacaine, tetracaine, trimecaine, menthol, eugenol and safe pharmaceutical formulations of tetrodotoxin, saxitoxin, and neosaxitoxin.

The stomach is a highly acidic environment, which has strong effects on transport and passage of compounds through the stomach wall. Chloroprocaine and procaine are examples of local anesthetics which have a primary amine in their structure. The strong protonation of the molecule in the acidic layer near the stomach wall may hinder further passage through the mucus epithelial cells. Local anesthetics without primary amino group, or a secondary amino group instead of a primary amino group may be less hindered in passage through the stomach wall and therefor act at relatively lower doses. Such a group of local anesthetics with less hindrance in passage are a preferred group of local anesthetics according an aspect of the invention. Such a group of local anesthetics with less hindrance are ropivacaine, bupivacaine, tetracaine, mepivacaine and lidocaine, even more preferred are lidocaine and ropivacaine. Most preferred is lodacaine. Intermediate in this respect is prilocaine with two secondary amino functions.

A local anesthetic use according to aspects of the invention can optionally be combined with antioxidants to prevent myopathies. The disclosure also provides for the manufacture of a medicine comprising a local anesthetic drug of the treatment of anorexia, cachexia, sarcopenia, postoperative ileus and postoperative complications in food processing. The local anesthetic for the effect of the invention is preferably administered via the oral route of access to the surface to be influenced by the local anesthetic. Accordingly, in one embodiment the invention relates to orally administered anesthetics. Although the local anesthetic can be applied in solid form, it is preferably formulated in solution or suspension in a vehicle that allows the local anesthetic to penetrate into the tissue forming the surface of the pharyngeal, esophageal, gastric and/or duodenal tract. The formulation can be prepared to be most suitable for retention by the mucous surface of these parts of the feeding tract. Improvement of absorption by mucous tissue can be improved by penetration enhancers and by prolongation of the exposure time of the tissue to the drug. A viscous and hydrophilic vehicle facilitates retention of the formulation on the mucous surface. In an embodiment of the disclosure the local anesthetic is dissolved or suspended in a viscous solution of alginate. In another embodiment the local anesthetic is added to food. In another formulation solid particles of the local anesthetic are encapsulated in a taste masking composition and administered in a tablet, suspension or as food additive. The taste masking compositions should be made such that the taste protecting layer disintegrates or releases the local anesthetic near the surface to be influenced, for example by pH sensitivity. Polymers of methylaminoethyl-methacrylate and neutral methacrylate ester monomers (Eudragit E-100 and others) have such properties.

A suitable dosage is selected to obtain effective meal size increase or food retention with the selected local anesthetic drug and type of pharmaceutical formulation. The exact dose depends on the local anesthetic drug selected for use. Factors relating to the characteristics of the pharmaceutical formulation, the type and severity of the disorder, and the age of the patient should be taken into account in dose selection. Since the local anesthetic is not applied by injection into the tissue but influences the tissue by exposure of the surface to the drug, the amount of drug needed for the effect according to the invention is usually at the higher end of the dose range which is known to be effective for the particular selected local anesthetic drug. Preferred concentrations for lidocaine and ropivacaine are 20 mg/ml fluid and 7.5-11.25 mg/ml fluid, respectively. Preferred concentration for ropivacaine is 7.5 mg/ml.

The treatment with the local anesthetic drug should be given shortly before, within or shortly after a meal in order to have the effect of interfering with physiological signals which would otherwise terminate a meal or would lead to expulsion of food by vomiting. The time before the meal should be determined by what is customary for the duration of action of a local anesthetic. The onset and duration of action of the selected local anesthetic drugs determine the suitable time of administration. An administration between an hour, preferably half an hour and shortly before a meal is suitable for the effect according to the invention, for example 60, 30, 25, 20, 15, 10, 5 minutes before a meal is preferred, and more preferred is 18, 15, 12, 9 or 6 minutes before initiating a meal. When the local anesthetic is administered after a meal this should preferably be done immediately after a meal. Some delay may be introduced, but in general the administration after a meal is preferably within the period from 0 to 30 minutes after termination of a meal, possibly 5, 10, 15, 20 or 25 minutes after termination of a meal.

As indicated here before the effect of the invention might be due to facilitating filling and distension of the stomach by inhibiting signals from stretch or even pain receptors. Such a mechanism will operate more effectively at early stages, or even at the first administration only, of a series of administrations, in view of a persisting effect on the capacity of the stomach to distend without inducing signals of excessive distension or even pain. This means that a single treatment i.e. a single, or alternatively, a few, say, 2, 3 or 4 administrations, are preferred and separate embodiments of the invention.

Treatment with local anesthesia of the pharyngeal-esophageal-gastric-duodenal tract can be combined with instructions and advice on life regimes with dietary and behavioral instructions and advice. More intake of nutrient-rich food and energy expending exercises (resistance and endurance training) in combination with the enhanced intake effect by local anesthesia will optimally improve the condition of patients suffering from the consequences of reduced food intake. In circumstances of postoperative care the use according to the invention can be combined with advice on intake of food that may be less attractive for appetite, but is more suitable for the gastro-intestinal system for recovery of intestinal functioning.

The terms used in this specification are used according to their usual meaning in medical practice. In case of doubt our use of the terms can be further understood as follows.

The surface of the pharynx, esophagus, stomach or duodenum is the tissue facing the lumen of the pharynx, esophagus, stomach or duodenum and which comprises the epithelium and deeper layers which may comprise autonomic musculature and myenteric nerve plexi.

A meal is a short time period of food intake. Taking a snack or small quantity is having the same meaning as a meal, but the meaning of the term meal does not extend to intake of a candy or goody merely selected for pleasure, irrespective of its nutritive quality. A meal is started by a decision of the subject to be treated or by the physician or other person supporting the said subject in taking a meal, and having food available. A meal is terminated by a decision of the subject to be treated or by the physician or other person supporting the said subject in taking a meal or the meal is terminated upon termination of the period of availability of food for the subject to be treated.

Facilitation of food intake and food retention does not only mean an increase in the volume of a meal, but also of an increase in the total volume of food intake during a within-one-day interval by shortening of intermeal interval(s) or shortening of time spent on a meal with concomitant increase in frequency of meals. Food intake can be considered facilitated if a meal is taken more rapidly compared to untreated individuals or if it is prevented that food is expulsed by vomiting.

Food in the present context does not necessarily mean appetitive nutritious solid matter, but may also be in fluid form and may have a non-nutritious composition or may not necessarily be appetitive. The latter circumstances may arise in the context of a need of intake of medically useful non-nutritious filling material in the intestinal system or food having become less attractive due to supplements for therapeutic effects. The intake of such food can be aided by using the effect obtained by using the present invention.

EXAMPLES

Methods General

In the following examples food intake tests were run with cohorts of 32 Wistar rats having food intake sessions in two groups of 16 rats in parallel. There were 8 rats per experimental group. The rats weighed in the range of 260-370 grams. Rats were acclimatized to the housing conditions in our laboratory for at least one week after arrival from the breeder. The rats were housed in pairs in Macrolon cages of 42×26 cm and 15 cm high, with standard food and water available ad libitum. The day-night cycle was not reversed (lights on at 7:00 AM, off 19:00 PM). Food intake tests were run in the same room wherein the rats were housed in the light period of the diurnal cycle of the rats. In a further period the rats were habituated to human handling and to the manner of presentation of mealworms in the food intake tests. Food intake was measured with rats without food deprivation. Food intake tests were done by placing the rats from their home cage individually into clean Macrolon (42×26×15 cm) cages without bedding. A weighed amount of at least 15-20 g living mealworms in a petri dish was placed in the middle of the cage and rats were allowed 30 minutes for eating mealworms. During the 30 minute test for food intake no drinking water was available. Injection treatments were administered at determined times before the food intake test. After drug administration the rats were returned to their home cage. Both rats of a pair in a living cage were assigned to the same treatment groups. Otherwise allocation of rats to experimental groups was done such that the treatments were equally and randomly spread over the duration of an experiment. The experimenter remained in the test room for the duration of an experiment. This allowed observation of general behavioural effects of the treatments. Abnormalities were recorded.

The use of rats in several tests, separated at least one week was not excluded.

Drugs

For drug administration commercially available stock solutions in vials were used:
lidocainehydrochloride 20 mg/ml injection fluid (Fresenius Kabi); procainamidehydrochloride 100 mg/ml injection fluid (Apotheek Haagse Ziekenhuizen);
ropivacainehydrochloride 7.5 mg/ml injection fluid (Fresenius Kabi);
metoclopramine (Sigma) was weighed and dissolved for use.

Drugs were administered in volumes of 1 ml/kg rat.

Vehicle: for local anesthetics the commercial physiological saline solutions for injection were used directly or the solution was diluted with distilled water. Alginate for a 2% viscous alginate solution was added 18 hours before use of the solution for injection. The solution was prepared to a viscous solution by allowing 18 hours of slow mechanical mixing.

Metoclopramide was dissolved in physiological saline.

For administration of the drug into the lumen of the esophagus the injection fluid was administered by entering a thick needle with rounded tip via, and into the esophagus just above the lower esophageal sphincter and retreating during injection to release the volume to be injected just behind the pharynx. The stainless steel needle for injection into the esophagus was 26 mm long, 1 mm thick and had a rounded thickened tip of 2 mm diameter.

For administration into the stomach a similar 1 mm thick needle with a 2 mm tip and 60 mm length was introduced into the stomach via the esophagus as customary for oral administration in rats.

For administration subcutaneously (sc) the injection fluid was injected with a sharp thin needle under the skin in the neck.

Although we do not base our conclusions entirely on statistical tests, P values are reported as obtained with independent two-sided Student's t-tests for equal variances.

Example 1: Effect of Doses 1-10 mg/kg of Lidocaine into the Esophagus

Groups:
A: Placebo 1 ml/kg esophagus
B: Lidocaine.HCl 1 mg/kg esophagus
C: Lidocaine.HCl 3 mg/kg esophagus
D: Lidocaine.HCl 10 mg/kg esophagus Rats weighed 290-365 g rats. Treatments were administered 30 minutes before the start of the food intake test. The data of one rat in the 1 mg/kg lidocaine group were accidentally lost. Grams of mealworms eaten (AVG is average of group; SEM is standard error of the mean; N is number of rats per group; significance refers with * to <0.05 and ** to <0.01

|  | placebo 1 ml/kg esophagus | Lidocaine•HCl 1 mg/kg esophagus | Lidocaine•HCl 3 mg/kg esophagus | Lidocaine•HCl 10 mg/kg esophagus |
|---|---|---|---|---|
| AVG | 15.38 | 14.85 | 14.46 | 14.54 |
| SEM | 0.22 | 0.54 | 0.49 | 0.54 |
| N | 8 | 7 | 8 | 8 |
| p-value |  | 0.3531 | 0.1059 | 0.1708 |
| significance |  |  |  |  |

Conclusion: the dose of the anesthetic lidocaine in this procedure should be above 10 mg/kg

Example 2: Effect of Dose of 20 mg/kg of Lidocaine.HCl into Stomach or Esophagus Groups:
A: Placebo 1 ml/kg esophagus
B: Lidocaine.HCl 20 mg/kg esophagus 30 minutes before start of food intake test
C: Lidocaine.HCl 20 mg/kg stomach 30 minutes before start of food intake test
D: Lidocaine.HCl 20 mg/kg esophagus 15 minutes before start of food intake test Rats weighed 262-371 g rats. Treatments were administered 15 (Group D) or 30 (Groups A-C) minutes before the start of the food intake test.
Grams of Mealworms Eaten

|  | placebo 1 ml/kg esophagus | Lidocaine•HCl 20 mg/kg esophagus | Lidocaine•HCl 20 mg/kg stomach | Lidocaine•HCl 20 mg/kg esophagus 15 min |
|---|---|---|---|---|
| AVG | 14.08 | 17.14 | 16.28 | 16.91 |
| SEM | 0.89 | 0.72 | 0.51 | 0.72 |
| N | 8 | 8 | 8 | 8 |
| p-value |  | 0.0186 | 0.0498 | 0.0267 |
| significance |  | * | * | * |

Conclusion: The dose of 20 mg/kg lidocaine is effective. The application in the esophagus is more effective than application into the stomach.

Example 3: The Effect of Procainamide and Ropivacaine into the Esophagus on Food Intake Groups:
A: Placebo 1 ml/kg esophagus
B: Procainamide 20 m/kg esophagus
C: Ropivacaine 1.25 mg/kg esophagus Data of group D are not relevant in this context.

Rats weighed 268-310 grams. Treatments were administered 30 minutes before the start of the food intake test.
Grams of Mealworms Eaten

|  | placebo 1 ml/kg esophagus | Procainamide 20 m/kg esophagus | Ropivacaine 1.25 mg/kg esophagus |
|---|---|---|---|
| AVG | 12.63 | 12.11 | 13.40 |
| SEM | 0.87 | 1.30 | 0.71 |
| N | 8 | 8 | 8 |
| p-value |  | 0.7417 | 0.5090 |
| significance |  | // | // |

Conclusion: The dose of procainamide should be higher than 20 mg/kg in this procedure; The dose of ropivacaine should be higher than 1.25 mg/kg in this procedure.

Example 4: The Effect of 100 mg/kg Procainamide and 3.75 and 7.5 mg/kg into the Esophagus on Food Intake A: Placebo 1 ml/kg esophagus
B: Procainamide 100 m/kg esophagus
C: Ropivacaine 3.75 mg/kg esophagus
D: Ropivacaine 7.5 mg/kg esophagus Rats weighed 258-309 grams. Treatments were administered 30 minutes before the start of the food intake test
Grams of Mealworms Eaten

|  | placebo 1 ml/kg esophagus | Procainamide 100 m/kg esophagus | Ropivacaine 3.75 mg/kg esophagus | Ropivacaine 7.5 mg/kg esophagus |
|---|---|---|---|---|
| AVG | 11.53 | 10.55 | 12.08 | 13.58 |
| SEM | 1.11 | 0.77 | 0.69 | 0.77 |
| N | 8 | 8 | 8 | 8 |
| p-value |  | 0.4816 | 0.6792 | 0.1517 |
| significance |  | // | // | // |

Conclusion: Ropivacaine enhanced food intake in this procedure at 7.5 mg/kg in the esophagus.

Example 5: Ropivacaine in Stomach or Esophagus

Groups:
A: Placebo 1 ml/kg esophagus
B: Ropivacaine 7.5 mg/kg esophagus
C: Ropivacaine 11.25 mg/kg esophagus
D: Ropivacaine 7.5 mg/kg stomach
  Rats weighed 292-337 grams
  Grams of Mealworms Eaten

|  | placebo 1 ml/kg esophagus | Ropivacaine 7.5 mg/kg esophagus | Ropivacaine 11.25 mg/kg esophagus | Ropivacaine 7.5 mg/kg stomach |
| --- | --- | --- | --- | --- |
| AVG | 12.45 | 13.24 | 14.44 | 10.72 |
| SEM | 1.24 | 0.67 | 0.84 | 0.96 |
| N | 8 | 8 | 8 | 8 |
| p-value |  | 0.5830 | 0.2046 | 0.2878 |
| significance |  | // | // | // |

Conclusion: Ropivacaine in the esophagus at 7.5 mg/kg and 11.25 mg/kg is effective in increasing meal size, in particular when administered in the esophagus. The difference between amount eaten by groups B (esophagus) and D (stomach) is having a P value<0.01 (Significance **).

Example 6: Effect of Subcutaneous Metoclopramide at 3, 10 and 30 mg/kg

Groups:
A: Placebo 0.9% NaCl 1 ml/kg sc
B: 3 mg/kg sc metoclopramide
C: 10 mg/kg sc metoclopramide
D: 30 mg/kg sc metoclopramide Rats weighed 284-332 grams. Treatments were administered 30 minutes before the start of the food intake test.
Grams of Mealworms Eaten

|  | placebo 0.9% NaCl 1 ml/kg sc | metoclopramide 3 mg/kg sc | metoclopramide 10 mg/kg sc | metoclopramide 30 mg/kg sc |
| --- | --- | --- | --- | --- |
| AVG | 15.69 | 11.86 | 1.25 | 0.22 |
| SEM | 0.76 | 0.83 | 0.15 | 0.05 |
| N | 8 | 8 | 8 | 8 |
| p-value |  | 0.0043 | 0.0001 | 0.0001 |
| significance |  |  |  | ** |

Conclusion: Metoclopramide subcutaneously at doses above 3 mg/kg inhibits food intake.

Example 7: Effect of Subcutaneous Metoclopramide at 0.1-1 mg/kg

Groups:
A: placebo 0.9% NaCl 1 ml/kg sc
B: 0.1 mg/kg sc metoclopramide
C: 0.3 mg/kg sc metoclopramide
D: 1 mg/kg sc metoclopramide Rats weighed 295-356 grams. Treatments were administered 30 minutes before the start of the food intake test
Grams of Mealworms Eaten

|  | placebo 0.9% NaCl 1 ml/kg sc | metoclopramide 0.1 mg/kg sc | metoclopramide 0.3 mg/kg sc | metoclopramide 1 mg/kg sc |
| --- | --- | --- | --- | --- |
| AVG | 12.26 | 13.51 | 12.23 | 15.76 |
| SEM | 1.16 | 0.76 | 1.41 | 0.54 |
| N | 8 | 8 | 8 | 8 |
| p-value |  | 0.3791 | 0.9882 | 0.0159 |
| significance |  | // | // | * |

Conclusion: Subcutaneous injection of 1 mg/kg metoclopramide increases food intake. 0.1 and 0.3 mg/kg subcutaneously are ineffective in this procedure.

The invention claimed is:
1. A method of increasing the amount of food eaten by a mammal after surgery on the intestinal tract below the stomach or after caesarian section in said mammal, the method comprising having the mammal:
  a) ingest a local anesthetic drug such that the local anesthetic drug is applied to a surface of the esophagus and/or stomach of said mammal; and
  b) eat a meal, wherein the local anesthetic drug is ingested before or during eating said meal, wherein the local anesthetic drug causes an amount of the meal eaten by the mammal to increase.
2. The method according to claim 1, wherein the local anesthetic drug is selected from the list consisting of amethocaine, articaine, benzocaine, bupivacaine, chloroprocaine, cinchocaine, cyclomethycaine, dibucaine, etidocaine, larocaine, levobupivacaine, lidocaine, mepivacaine, novocaine, piperocaine, prilocaine, proparacaine, propoxycaine, QX-222, QX-314, ropivacaine, tetracaine, trimecaine, eugenol, tetrodotoxin, saxitoxin, and neosaxitoxin.
3. The method according to claim 1, wherein the local anesthetic drug is lidocaine or ropivacaine.
4. The method according to claim 1, wherein the local anesthetic drug is applied to a surface of the esophagus.
5. The method according to claim 1, wherein the local anesthetic drug is applied to a surface of the stomach.
6. The method according to claim 1, wherein the drug is formulated in a solution or suspension in a vehicle that facilitates retention of the formulation by a mucous epithelium of a mammal.
7. The method according to claim 6, wherein the local anesthetic drug is dissolved or suspended in a solution of alginate.
8. The method according to claim 1, wherein the local anesthetic drug comprises lidocaine or ropivacaine and is applied to a surface of the esophagus.
9. The method according to claim 1, wherein the local anesthetic drug comprises lidocaine or ropivacaine and is applied to a surface of the stomach.
10. The method according to claim 1, wherein the local anesthetic drug is administered within 30 minutes before eating.
11. The method according to claim 2, wherein the local anesthetic drug is applied to a surface of the esophagus.
12. The method according to claim 2, wherein the local anesthetic drug is applied to a surface of the stomach.
13. The method according to claim 2, wherein the drug is formulated in a solution or suspension in a vehicle that facilitates retention of the formulation by a mucous epithelium of a mammal.
14. The method according to claim 13, wherein the local anesthetic drug is dissolved or suspended in a solution of alginate.

15. The method according to claim 2, wherein the local anesthetic drug comprises lidocaine or ropivacaine and is applied to a surface of the esophagus.

16. The method according to claim 2, wherein the local anesthetic drug comprises lidocaine or ropivacaine and is applied to a surface of the stomach.

17. The method according to claim 2, wherein the local anesthetic drug is administered within 30 minutes before eating.

18. The method according to claim 12, wherein the local anesthetic drug is administered as a tablet.

19. The method according to claim 18, wherein the tablet comprises the local anesthetic drug encapsulated in a taste masking composition to form a taste-protecting outer layer of the tablet, wherein the taste-protecting layer disintegrates or releases the local anesthetic drug near the surface of the stomach.

20. The method according to claim 16, wherein the local anesthetic drug is administered as a tablet.

21. The method according to claim 20, wherein the tablet comprises the local anesthetic drug encapsulated in a taste masking composition to form a taste-protecting outer layer of the tablet, wherein the taste-protecting layer disintegrates or releases the local anesthetic drug near the surface of the stomach.

\* \* \* \* \*